| United States Patent [19] | [11] Patent Number: 4,882,164 |
|---|---|
| Ferro et al. | [45] Date of Patent: Nov. 21, 1989 |

[54] PARENTERAL MICELLE SOLUTIONS

[75] Inventors: Alberto Ferro, Riehen; Hans Steffen, Liestal, both of Switzerland

[73] Assignee: Hoffmann-La Roche Inc., Nutley, N.J.

[21] Appl. No.: 144,997

[22] Filed: Jan. 19, 1988

[30] Foreign Application Priority Data

Feb. 3, 1987 [CH] Switzerland .......................... 380/87

[51] Int. Cl.$^4$ ...................... A61K 37/20; G01N 33/92
[52] U.S. Cl. ....................................... 424/450; 264/46; 428/402.2; 436/71; 436/829; 514/772; 514/784
[58] Field of Search .................. 424/450; 436/829, 71; 264/4.6; 428/402.2; 514/772, 784

[56] References Cited

U.S. PATENT DOCUMENTS

| 3,197,368 | 7/1965 | Lappe et al. ........................ 260/403 |
| 3,896,145 | 7/1975 | Berger et al. ........................ 260/315 |
| 4,158,707 | 6/1979 | Steffen et al. ....................... 514/772 |
| 4,271,196 | 6/1981 | Schmidt .............................. 514/786 |
| 4,328,222 | 5/1982 | Schmidt .............................. 514/786 |
| 4,649,155 | 3/1987 | Steffen et al. ....................... 514/458 |

FOREIGN PATENT DOCUMENTS

| 3221579A1 | 12/1983 | Fed. Rep. of Germany . |
| 1587076 | 7/1977 | United Kingdom . |
| 2046145 | 4/1980 | United Kingdom . |

OTHER PUBLICATIONS

T. R. Bates et al., Jour. of Pharm. Sci., No. 9, pp. 901–906 (Sep. 1986).

Primary Examiner—William R. Dixon, Jr.
Assistant Examiner—Anthony J. Green
Attorney, Agent, or Firm—Jon S. Saxe; Bernard S. Leon; William G. Isgro

[57] ABSTRACT

Aqueous mixed micelle solutions comprising cholanic acid salts and lipids used for the solubilization of non-steroidal anti-inflammatories and for the preparation of locally tolerable pharmaceutical administration forms for such medicaments, are described.

9 Claims, No Drawings

PARENTERAL MICELLE SOLUTIONS

BRIEF SUMMARY OF THE INVENTION

The invention relates to aqueous mixed micelle solutions containing a salt of a cholanic acid, a lipid and a non-steroidol anti-inflammatory.

DETAILED DESCRIPTION OF THE INVENTION

Local irritations and haemolytic effects are frequently observed with the parenteral administration of non-steroidal anti-inflammatories. The object of the present invention is to make available a more tolerable parenteral application form for non-steroidal anti-inflammatories.

It is known from German Offenlegungsschrift No. 2 730 570 to use mixed micelles from cholanic acids and lipids for the solubilization of difficultly soluble or non-water soluble pharmaceutically active substances in an aqueous medium. It has surprisingly been found that aqueous mixed micelle solutions of non-steroidal anti-inflammatories are substantially more tolerable in the case of parenteral administration than aqueous-organic or even purely aqueous solutions of such anti-inflammatories which have not been manufactured using mixed micelles.

The present invention is concerned with aqueous mixed micelle solutions containing a salt of a cholanic acid, a lipid and a non-steroidal anti-inflammatory.

In another aspect the invention is concerned with the use of mixed micelles from cholanic acid salts and lipids for the solubilization of non-steroidal anti-inflammatories in aqueous media.

As cholanic acid salts there come into consideration in the present mixed micelle solutions the salts of cholanic acids or cholanic acid derivatives which are mentioned in DE-OS 2 730 570, especially cholates, glycocholates and taurocholates, especially the alkali salts such as the sodium salts. Sodium glycocholate is especially preferred.

As lipids, there come into consideration especially phosphatidylcholines, for example, natural lecithins or synthetic lecithins having modified side-chains, for example, those which are described in European Patent Application A2-0154977. Natural lecithins such as egg lecithin or soya lecithin are preferred.

Non-steroidal anti-inflammatories (non-steroidal anti-inflammatory drugs, NSAID's) in the sense of this invention are compounds which are structurally different from steroids and which display an anti-inflammatory activity. Such compounds are frequently characterized by the presence of a carboxylic acid group and/or are derivatives of acetic acid or of propionic acid. Examples of such non-steroidal anti-inflammatories are carprofen, ibuprofen, benoxaprofen, naproxen, sulindac, zomepirac, fenclofenac, alclofenac, ibufenac, flunixin, indomethacin or salts thereof. A preferred non-steroidal anti-inflammatory in the scope of the present invention is carprofen (6-chloro-α-methyl-carbazole-2-acetic acid) and physiologically compatible salts thereof with bases, for example, alkali metal hydroxides, amines or basic amino acids such as arginine or lysine.

The molar ratio between lipid and the cholanic acid conveniently lies in the order of 0.1:1 to 2:1. Mixture ratios of 0.8:1 to 1.5:1 are preferred.

The amount of lipid plus cholanic acid in the injection solution can vary over wide limits and can amount to, for example, 50–300 mg/ml of injection solution.

The amount of the pharmacon in the solutions in accordance with the invention can also vary over wide limits and can amount to, for example, 0.1–100 mg/ml of solution. By means of the solutions in accordance with the invention relatively large amounts of active substance can be solubilized in a volume unit, which is especially advantageous in the treatment of large animals.

The mixed micelle solutions in accordance with the invention can be prepared by simply mixing the individual ingredients. In another embodiment the lipid, the cholanic acid and a base suitable for forming a salt therewith, for example, an alkali hydroxide, or directly the cholanic acid salt as well as the active substance can be dissolved in an organic solvent, thereupon the organic solvent can be removed by evaporation and thereafter water, optionally isotonizing additives and, if desired, additional ingredients can be added, whereby as a rule the isotonizing additives and in most cases also the optional additional ingredients are admixed with the water prior to the addition to the mentioned evaporation residue. As organic solvents, there come into consideration those in which the components to be solubilized are sufficiently soluble, such as, for example, lower alkanols, especially methanol or ethanol.

In a further embodiment, an aqueous mixed micelle solution can be prepared firstly from a lipid and a cholanic acid salt and then the active substance can be added.

The time after stirring which is required until the thus-obtained mixture becomes homogeneous depends on the type of cholanic acid, lipid, active substance and the concentrations thereof and as a rule can be shortened by warming for a brief period.

The mixed micelle solutions in accordance with the invention are conveniently adjusted to a pH value of about 5.5–7.5.

The mixed micelle solutions, in accordance with the invention, can contain additional adjuvants, for example, buffers, isotonizing additives, stabilizers and/or preserving agents, for example, benzyl alcohol. As isotonizing additives, there come into consideration especially: sodium chloride, mannitol or glucose. Tris buffer, phosphate buffer, citrate buffer, glycine buffer, citrate-phosphate mixed buffers and the like can be used as the buffer. The osmotic pressure of the injection solutions, in accordance with the invention, should in the ideal case correspond to that of the blood, that is, about 300 mOsm, but can vary in certain limits.

Furthermore, conveniently the preparation of the solutions, in accordance with the invention can be carried out under an atmosphere of inert gas and by adding to the solution an antioxidant such as, for example, sodium ascorbate, sodium hydrogen sulfite or sodium pyrosulfite.

A preferred mixed micelle solution, in accordance with the invention, contains sodium glycocholate, a natural lecithin and carprofen or a salt thereof, especially the arginine or lysine salt.

Such a solution is especially suitable for use in veterinary medicine, for example, for the treatment of acute and chronic laminitis; skeletal disorders such as navicular disease; myositis; pains in the case of colics, especially flatulence and spastic colic; pains in the case of disorders of the respiratory tract; acute mastitis; and traumatic pains and for the treatment of disorders in the puerperal phase such as mastis, lacking of or insufficient uterus involution (postpartum involution).

The following Examples further illustrate the invention.

EXAMPLE 1

(a) 8.85 g of glycocholic acid are suspended in 50 ml of N$_2$-gassed water for injection and dissolved with the aid of 1.9 ml of freshly prepared NaOH 40%.

(b) 16.9 g of finely divided lecithin are added thereto and dissolved while stirring well.

(c) The mixed micelle solution obtained is warmed to about 50°–60° C.

(d) 3 g of L-arginine are dissolved at about 40° C. in 15 ml of N$_2$-gassed water for injection.

(e) 5 g of carprofen substance are suspended in the mixed micelle solution (c) pre-warmed at about 50°–60° C. and dissolved with the portionwise addition of the L-arginine solution (d).

(f) The solution obtained is adjusted to pH 6.0±0.2 with 2N HCl and made up to the final volume of 100 ml with N$_2$-gassed water for injection.

(g) The solution is filtered through a membrane filter of 0.45 μm, filled into ampules under aseptic conditions and a N$_2$ atmosphere and sterilized in an autoclave.

EXAMPLE 2

The procedure of Example 1 is repeated, but 1.5 g of benzyl alcohol are added after operation (e).

EXAMPLE 3

9.86 g of glycocholic acid (containing 5.6% of water) and 3.48 g of L-arginine are dissolved in 60 ml of ethanol-water (2:1) at about 40° C. Thereafter, 17.77 g of lecithine are added thereto and dissolved. The organic solvent is evaporated in a rotating evaporator under reduced pressure whereby a foam is formed. Four (4.0) g of indomethacin and 1.95 g of L-arginine are dissolved at room temperature in 55 ml of N$_2$-gassed water. The solution obtained is added to the foam obtained above and the mass is dissolved with stirring. The mixed micelle solution obtained is adjusted to pH 7.1±0.1 with 2N HCl and made up to a final volume of 100 ml with N$_2$-gassed water for injection. Thereafter, one proceeds according to Example 1 (g).

EXAMPLE 4

9.86 g of glycocholic acid (containing 5.6% of water) and 3.48 g of L-arginine are dissolved in 50 ml of N$_2$-gassed water for injection. Thereafter, one proceeds according to Example 1 (b) and (c) adding, however, 17.77 g of lecithin. 2.5 g of ibuprofen and 2.11 g of L-arginine are dissolved in 20 ml of methanol, whereupon the methanol is removed in a rotatory evaporator. The so-obtained powder is added to the mixed micelle solution and dissolved with stirring. The solution is then adjusted to pH 7.1±0.1, made up to a final volume of 100 ml with N$_2$-gassed water for injection and filled into ampules as in Example 1 (g).

EXAMPLE 5

9.86 g of glycocholic acid (containing 5.6% of water) and 3.48 g of L-arginine are dissolved in 50 ml of N$_2$-gassed water for injection. Thereafter, 2.5 g of naproxen and 1.89 g of L-arginine are added to the solution obtained and dissolved with stirring. Then, 17.77 g of finely divided lecithin are added to the solution and dissolved with stirring at about 40°–50° C. Thereafter, the pH is adjusted as in Example 3, the solution made up to a volume of 100 ml, filtered in filled into ampules.

EXAMPLE 6

In order to test the local tolerance, preparations A (control), B (formulation in accordance with the invention), C and D (conventional formulations) were administered intravenously once daily to dogs during 14 days.

| | | | |
|---|---|---|---|
| A | NaCl 0.9% | | |
| B | Carprofen | | 50.0 mg |
| | L-Arginine | | 30.0 mg |
| | Glycocholic acid (anhydrous) | | 88.5 mg |
| | NaOH 40% | | 19.0 μl |
| | Lecithin for mixed micelles | | 169.0 mg |
| | HCl (2N, pH 6.0) | | q.s |
| | Water for injection | ad | 1.0 ml |
| C | Carprofen | | 10.0 mg |
| | Polyethylene glycol 400 | | 600.0 μl |
| | Water for injection | ad | 1.0 ml |
| D | Carprofen | | 25.0 mg |
| | Diethanolamine | | 19.0 mg |
| | EDTA disodium salt | | 0.1 mg |
| | Benzyl alcohol | | 10.0 μl |
| | Water for injection | ad | 1.0 ml |

The medicated animals received 20 mg/kg of active substance. The injections were carried out each time at the same site (V. cephalica antebrachii).

RESULTS

In the case of the animal treated with C, an inflammation at site of administration appeared after 3 injections and the vein became closed after 6 injections.

In the case of the animal treated with D, the site of administration became inflamed even after the first administration. A third administration was not possible because of an obliteration of the veins. In the case of the animal treated with B and in the case of the control animal (A) no changes at the site of administration became evident after 14 injections. Upon autopsy, thrombophlebitis at the site of injection was evident in the case of animals treated with C and D; the animal treated with B was negative.

We claim:

1. Aqueous mixed micelle solutions consisting essentially of a salt of a cholanic acid, a lipid, an effective amount of a non-steroidal anti-inflammatory compound which is a carboxylic acid derivative, wherein the molar ratio between the lipid and the cholanic acid is in the range of from 0.1:1 to 2:1.

2. A mixed micelle solution, in accordance with claim 1, in which the cholanic acid is cholic acid, glycocholic acid or taurocholic acid.

3. A mixed micelle solution, in accordance with claim 2, in which the lipid is a phosphatidylcholine.

4. A mixed micelle solution, in accordance with claim 3, in which the lipid is a natural lecithin.

5. A mixed micelle solution, in accordance with claim 3, in which the non-steroidal anti-inflammatory is an acetic acid or propionic acid derivative.

6. A mixed micelle solution, in accordance with claim 5, in which the non-steroidal anti-inflammatory is carprofen, ibuprofen, benoxaprofen, naproxen, sulindac, zomepirac, fenclofenac, alclofenac, ibufenac, flunixin, indomethacin or a salt thereof.

7. A mixed micelle solution, in accordance with claims 5, in which the non-steroidal anti-inflammatory is carprofen.

8. A mixed micelle solution, in accordance with claim 1, containing sodium glycocholate, a natural lecithin and carprofen.

9. Aqueous mixed micelle solutions consisting essentially of a salt of a cholanic acid, a lipid, an effective amount of a non-steroidal anti-inflammatory compound which is a carboxylic acid derivative, wherein the molar ratio between the lipid and the cholanic acid is in the range of from 0.1:1 to 2:1, and at least one adjuvant.

* * * * *

UNITED STATES PATENT AND TRADEMARK OFFICE
CERTIFICATE OF CORRECTION

PATENT NO. : 4,882,164

DATED : November 21, 1989

INVENTOR(S) : Alberto Ferro and Hans Steffen

It is certified that error appears in the above-identified patent and that said Letters Patent is hereby corrected as shown below:

In Column 5, line 2, claim 7, delete "5" and insert -- 6 --.

Signed and Sealed this

First Day of January, 1991

Attest:

HARRY F. MANBECK, JR.

*Attesting Officer*   *Commissioner of Patents and Trademarks*